(12) United States Patent
Kubota et al.

(10) Patent No.: US 7,312,025 B2
(45) Date of Patent: Dec. 25, 2007

(54) METHODS AND SYSTEMS FOR EXTENDED IN VITRO CULTURE OF NEURONAL CELLS

(75) Inventors: Ryo Kubota, Seattle, WA (US); Thomas A Reh, Seattle, WA (US); Andrew J Fischer, Hilliard, OH (US)

(73) Assignee: University of Washington, Seattle, WA (US)

( * ) Notice: Subject to any disclaimer, the term of this patent is extended or adjusted under 35 U.S.C. 154(b) by 554 days.

(21) Appl. No.: 10/618,076

(22) Filed: Jul. 11, 2003

(65) Prior Publication Data

US 2004/0147019 A1  Jul. 29, 2004

Related U.S. Application Data

(60) Provisional application No. 60/395,973, filed on Jul. 12, 2002.

(51) Int. Cl.
*C12N 5/06* (2006.01)
*C12Q 1/00* (2006.01)
*C12Q 1/02* (2006.01)

(52) U.S. Cl. .................... 435/4; 435/347; 435/368; 435/373

(58) Field of Classification Search .............. None
See application file for complete search history.

(56) References Cited

U.S. PATENT DOCUMENTS

| | | | |
|---|---|---|---|
| 4,533,635 A | 8/1985 | Guédon born Saglier et al. | |
| 5,641,750 A | 6/1997 | Louis | |
| 5,736,516 A | 4/1998 | Louis | |
| 5,753,506 A | 5/1998 | Johe | |
| 5,840,686 A | 11/1998 | Chader et al. | |
| 5,851,832 A | 12/1998 | Weiss et al. | |
| 5,968,829 A | 10/1999 | Carpenter | |
| 6,040,180 A | 3/2000 | Johe | |
| 6,048,728 A | 4/2000 | Inlow et al. | |
| 6,090,624 A | 7/2000 | Greenwood et al. | |
| 6,117,675 A | 9/2000 | van der Kooy et al. | |
| 6,121,231 A | 9/2000 | Petit et al. | |
| 6,183,735 B1 | 2/2001 | Greenwood et al. | |
| 6,319,687 B1 | 11/2001 | Chader et al. | |
| 6,376,238 B1 | 4/2002 | Watanabe | |
| 6,379,882 B1 | 4/2002 | Bitler et al. | |
| 6,406,840 B1 | 6/2002 | Li et al. | |
| 6,423,504 B1 | 7/2002 | Tanaka et al. | |
| 6,498,108 B2 | 12/2002 | Cao et al. | |
| 6,517,833 B2 | 2/2003 | Edge | |
| 2002/0009713 A1 | 1/2002 | Miller et al. | |

FOREIGN PATENT DOCUMENTS

| | | |
|---|---|---|
| EP | 1 130 096 A1 | 9/2001 |
| JP | 5-123168 | 5/1993 |
| JP | 6-90738 | 4/1994 |
| JP | 7-289249 | 11/1995 |
| JP | 9-295976 | 11/1997 |
| JP | 10-257891 | 9/1998 |
| JP | 11-32769 | 2/1999 |
| JP | 11-292774 | 10/1999 |
| JP | 2000-139470 | 5/2000 |
| JP | 2001-255318 | 9/2001 |
| JP | 2001-299334 | 10/2001 |
| WO | WO 97/01628 | 1/1997 |
| WO | WO 97/04733 | 2/1997 |
| WO | WO 98/12303 | 3/1998 |
| WO | WO 99/13074 | 3/1999 |
| WO | WO 99/29279 | 6/1999 |
| WO | WO 99/34834 | 7/1999 |
| WO | WO 00/29550 | 5/2000 |
| WO | WO 00/40699 | 7/2000 |
| WO | WO 00/47238 | 8/2000 |
| WO | WO 01/58460 A1 | 8/2000 |
| WO | WO 00/52143 | 9/2000 |
| WO | WO 01/09327 A2 | 2/2001 |
| WO | WO 01/42784 A2 | 6/2001 |
| WO | WO 01/81551 A2 | 11/2001 |
| WO | WO 01/83714 A2 | 11/2001 |
| WO | WO 02/29011 A2 | 4/2002 |
| WO | WO 02/076386 A2 | 10/2002 |

OTHER PUBLICATIONS

Aramant, R. et al., "Transplantation of Human Embryonic Retina to Adult Rat Retina," *Restor. Neurol. Nerutrosci.* 2(1):9-22, Oct. 1990.

Dentchev, T. et al., "Amyloid-β is Found in Drusen from Some Age-Related Macular Degeneration Retinas, but not in Drusen from Normal Retinas," *Molecular Vision* 9:184-190, Mar. 2003.

Fischer, A.. et al., "Identification of a Proliferating Marginal Zone of Retinal Progenitors in Postnatal Chickens," *Develop. Biol.* 220(2):197-200, Apr. 2000.

Fintz, A-C. et al., "Partial characterization of retina-derived cone neuroprotection in two culture models of photoreceptor degeneration," *Invest. Ophthal. & Vis. Sci.* 44(2):818-825, Feb. 2003.

(Continued)

*Primary Examiner*—Christina Chan
*Assistant Examiner*—Stephen Gucker
(74) *Attorney, Agent, or Firm*—Seed IP Law Group PLLC

(57) ABSTRACT

A cell culture system related to extended in vitro culture of mature neuronal cells and methods for preparing the cell culture system are provided. In a preferred embodiment the invention provides a cell culture system comprising a mixture of mature neuronal retinal cells and cells isolated from a ciliary body. Methods for identifying bioactive agents that alter neurodegeneration of neuronal retinal cells are also provided.

9 Claims, 4 Drawing Sheets

OTHER PUBLICATIONS

Enzmann, V. et al., "Alterations of sensory retinal explants exposed to choroidal melanoma cells ex vivo," *Graefe's Archive for Clinical and Experimental Ophthalmology*, 238:985-992, Dec. 2000.

Ahmad, Iqbal et al. "Identification of Neural Progenitors in the Adult Mammalian Eye," *Biochemical and Biophysical Research Communications 270*:517-521, 2000.

Coulombe, James N. et al. "Stimulation of Somatostatin Expression in Developing Ciliary Ganglion Neurons by Cells of the Choroid Layer," *The Journal of Neuroscience 11*(2):553-562, Feb. 1991.

Wentzek, L.A. et al. "Choroid Tissue Supports the Survival of Ciliary Ganglion Neurons in vitro," *The Journal of Neuroscience 13*(7):3143-3154, Jul. 1993.

Gage, F. et al., "Isolation, Characterization, and Use of Stem Cells From the CNS," *Annu. Rev. Neurosci 18*:159-192, 1995.

Gaudin, C. et al., "Survival and Regeneration of Adult Human and Other Mammalian Photoreceptors in Culture," *Invest. Ophthal. & Vis. Sci. 37*(11):2258-2268, 1997.

Heidinger, V. et al., "Ability of Retinal Müller Glial Cells to Protect Neurons Against Excitotoxicityt in Vitro Depends Upon Maturation and Neuron-Glial Interactions," *GLIA 25*:229-239, 1999.

Hicks D. et al., "Survival and Regeneration of Adult Human Photoreceptors in Vitro," *Brain Research 643*(1/2):302-305, Apr. 1994.

Johnson, L. et al., "The Alzheimer's Aβ-Peptide is Deposited at Sites of Complement Activation in Pathologic Deposits Associated with Aging and Age-Related Macular Degeneration," *Proc. Natl. Acad. Sci. USA 99*(18):11830-11835, Sep. 2002.

Luo, X. et al., "Selective Excitotoxic Degeneration of Adult Pig Retinal Ganglion Cells in Vitro," *Invest. Ophthal. & Vis. Sci. 42*(5):1096-1106, Apr. 2001.

Ogilvie, J. et al., "Growth Factors in Combination, but Not Individually, Rescue rd Mouse Photoreceptors in Organ Culture," *Exp. Neurol. 161*(2):676-685, Feb. 2000.

Picaud, S. et al., "Adult Human Retinal Neurons in Culture: Physiology of Horizontal Cells" *Invest. Ophthal. & Vis. Sci. 39*(13):2637-2648, Dec. 1998.

Santos, R. et al., "Cyclic AMP Increases the Survival of Ganglion Cell in Mixed Retinal Cell Cultures in the Absence of Exogenous Neutrophic Molecules, an Effect that Involves Cholinergic Activity," *Braz. J. Med. Biol. Res. 34*(12):1585-1593, 2001.

Seiler, M. et al., "Intact Sheets Of Fetal Retina Transplanted To Restore Damaged Rat Retinas," *Invest. Ophthal. & Vis. Sci. 39*(11):2121-2131, Oct. 1998.

Giasson, B. et al., "The Relationship Between Oxidative/Nitrative Stress and Pathological Inclusions in Alzheimer's and Parkinson's Disease," *Free Radical Biology & Medicine 32*(12):1264-1275, 2002.

Tropepe, V. et al., "Retinal Stem Cells in the Adult Mammalian Eye," *Science 17*:2032-2036, Mar. 2000.

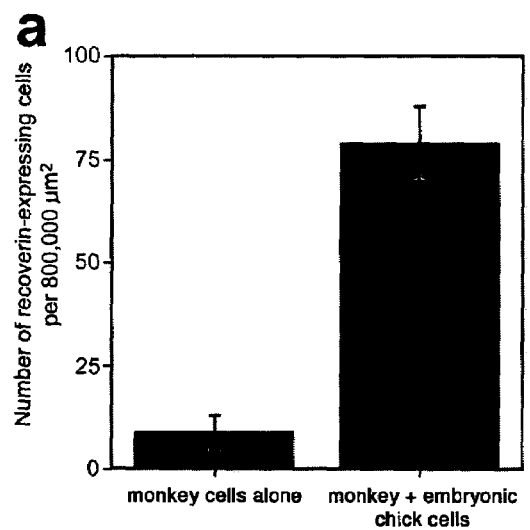
*FIG. 2A*
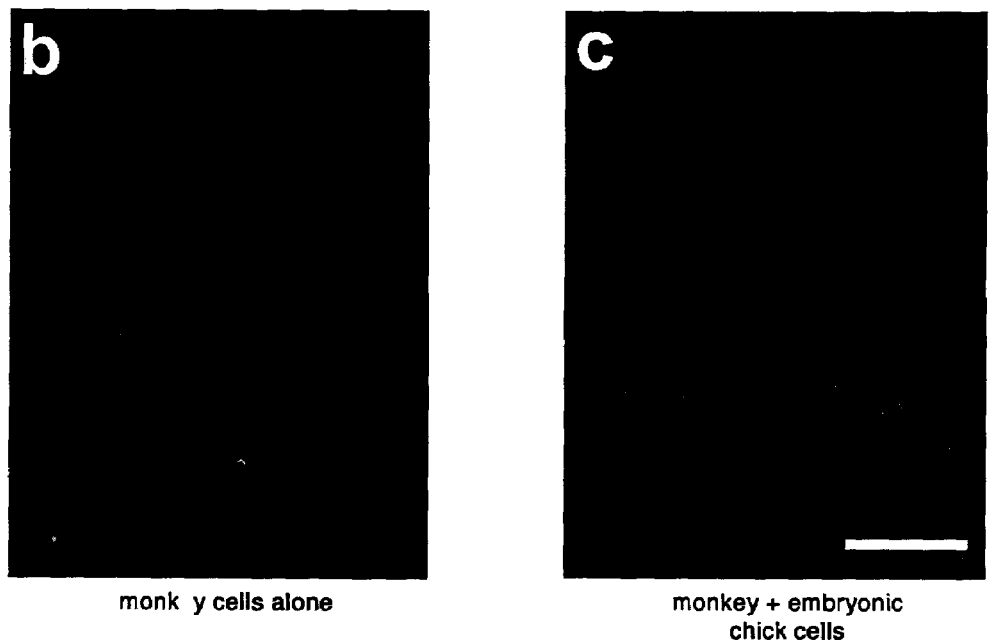
*FIG. 2B*     *FIG. 2C*

METHODS AND SYSTEMS FOR EXTENDED IN VITRO CULTURE OF NEURONAL CELLS

CROSS-REFERENCES TO RELATED APPLICATIONS

This application claims the benefit of U.S. Provisional Patent Application No. 60/395,973 filed Jul. 12, 2002, which is incorporated herein by reference in its entirety.

BACKGROUND OF THE INVENTION

1. Field of the Invention

The present invention relates generally to a cell culture system that provides extended in vitro culture of neuronal cells. The invention is particularly related to the extended culture of retinal neuronal cells. The cell culture system is useful for identifying bioactive agents that can be used for treating neurodegenerative diseases, particularly retinal diseases and disorders. The invention also relates to using the cell culture method for identifying cells that may be useful for treating a retinal degenerative disease or disorder.

2. Description of the Related Art

In vitro culture of neuronal cells in general, and of retinal neuronal cells in particular, has been problematic. For many years, it has been believed that fully mature neurons lack plasticity and the ability to repair and regenerate after injury. If mature central nervous system (CNS) neurons could be cultured and stimulated to regenerate, transplantation and functional restoration of damaged or diseased CNS tissue might become feasible.

As a first step, groups of investigators have been studying in vitro growth of CNS-derived neurons. Some of these studies involve transformed or immortalized neuronal cells; some cells have been derived from tumorigenic tissues. With respect to retinal cultures, in vitro retinal organ cultures, retinal explant cultures and retinal explant/membrane culture techniques have been reported. In addition, investigators have reported analysis of retinal neural cell cultures that are derived from embryonic tissue or embryonic stem cells or from neonatal retinas. However, the inability to accomplish long-term culture of post-mitotic neuronal cells has been a major roadblock within the field of neurobiology. If primary cells obtained from mature, fully-differentiated neuronal tissue in general, and mature retinal neurons in particular, could be cultured in vitro over an extended period of time, this would constitute a valuable tool for neurobiological studies including examination of cell-to-cell interactions; selection and analysis of neuroactive compounds and materials; provision of a controlled surrogate system for in vivo CNS and ophthalmic tests; and potential analysis single cells from a consistent population.

BRIEF SUMMARY OF THE INVENTION

Briefly stated, the present invention provides compositions and methods for extended cell culture of neuronal cells that may be used for identifying bioactive agents and cells useful for treatment of neurodegenerative diseases, including neurodegenerative retinal diseases and disorders. One aspect of the invention provides a cell culture system comprising a mixture of mature neuronal cells and cells isolated from a ciliary body. In certain embodiments of the invention the mature neuronal cells comprise mature retinal neuronal cells, wherein the mature retinal neuronal cells are bipolar cells, horizontal cells, amacrine cells, ganglion cells, and/or photoreceptor cells.

In another embodiment the invention provides a retinal cell culture system comprising a mixture of (i) mature retinal neuronal cells; (ii) cells isolated from a ciliary body; and (iii) embryonic retinal cells, wherein the mature retinal neuronal cells are bipolar cells, horizontal cells, amacrine cells, ganglion cells, and/or photoreceptor cells. In certain embodiments, the embryonic retinal cells comprise retinal stem cells and in certain other embodiments, the embryonic retinal cells comprise embryonic retinal progenitor cells.

The invention also provides a method for producing a retinal cell culture system comprising co-culturing a mature retinal neuronal cell and a cell isolated from a ciliary body. In another embodiment, a method is provided for enhancing survival of a mature retinal neuronal cell in vitro comprising co-culturing a mature retinal neuronal cell and a cell isolated from a ciliary body. In certain embodiments, these methods comprise co-culturing (i) a mature retinal neuronal cell; (ii) a cell isolated from a ciliary body; and (iii) an embryonic retinal cell. In certain specific embodiments, the embryonic retinal cell is selected from the group consisting of a retinal stem cell and an embryonic retinal progenitor cell.

The present invention also provides a method for identifying a bioactive agent that is capable of enhancing survival of a neuronal cell, comprising (i) contacting a candidate agent with the subject invention cell culture system as described herein under conditions and for a time sufficient to permit interaction between a neuronal cell of the cell culture system and the candidate agent; and (ii) comparing survival of a neuronal cell of the cell culture system in the presence of the candidate agent with survival of a neuronal cell of the cell culture system in the absence of the candidate agent, and therefrom identifying a bioactive agent that is capable of enhancing survival of the neuronal cell. In certain embodiments, the neuronal cell is a retinal neuronal cell.

In another embodiment, the invention provides a method for identifying a bioactive agent that is capable of inhibiting neurodegeneration of a neuronal cell comprising (i) contacting a bioactive agent with a cell culture system as described herein, under conditions and for a time sufficient to permit interaction between a neuronal cell of the cell culture system and the candidate agent; and (ii) comparing structure of a neuronal cell of the cell culture system in the presence of the bioactive agent with structure of a neuronal cell of the cell culture system in the absence of the bioactive agent, and therefrom identifying a bioactive agent that is capable of inhibiting neurodegeneration of the neuronal cell. In certain embodiments, the neuronal cell is a retinal neuronal cell.

The invention also provides a method for identifying a bioactive agent that is capable of treating a retinal disease comprising contacting a bioactive agent with the subject invention cell culture system as described herein, under conditions and for a time sufficient to permit interaction between a neuronal cell of the cell culture system and the candidate agent; and (ii) comparing neurodegeneration of a neuronal cell of the cell culture system in the presence of the bioactive agent with neurodegeneration of a neuronal cell of the cell culture system in the absence of the bioactive agent, and therefrom identifying a bioactive agent that is capable of treating a retinal disease. In certain embodiments, the neuronal cell is a retinal neuronal cell. In certain specific embodiments the retinal disease that is treated is macular degeneration, glaucoma, diabetic retinopathy, retinal detachment, retinal blood vessel occlusion, retinitis pigmentosa, or a retinal disorder associated with Alzheimer's disease.

In another embodiment, the invention provides a method for treating a retinal disease comprising introducing isolated retinal stem cells into retinal tissue of a subject in need thereof, wherein the retinal disease that is treated is macular degeneration, glaucoma, diabetic retinopathy, retinal detachment, retinal blood vessel occlusion, retinitis pigmentosa, or a retinal disorder associated with Alzheimer's disease.

Within one embodiment, the present invention provides methods for extended culture of mature neuronal cells that feature incubating mature neuronal cells with ciliary body cells. Within another embodiment, the invention provides an in vitro cell culture system that features a mixture of mature neuronal cells and a source of mature retinal stem cells. A ciliary body is a preferred source of retinal stem cells. In yet another embodiment, the invention provides a method for screening bioactive molecules, using an in vitro cell culture system containing a mixture of mature neuronal cells and ciliary body cells. While ciliary body cells are preferred for in vitro co-culture with mature neuronal cells, a source of stem cells, including other sources of CNS stem cells, may also find use within these methods and systems.

Although this invention is particularly amenable to the in vitro culture and survival of mature retinal neurons, the methods and systems disclosed are also useful for extended in vitro culture of other neuronal cell types obtained from a variety of species. The ciliary body cells (and/or a source of stem cells) and the neuronal cells need not be obtained from the same species. Further, the source of stem cells useful within the present invention may be primary cells; tumorigenic, transformed or immortalized cells; adult, embryonic or neonatal cells; or retinal or non-retinal cells.

These methods and systems may be used not only to culture retinal neurons in vitro, but also may find use with other central nervous system cells. Also, other mature, differentiated primary cells that are difficult to culture in vitro may be advantageously co-cultured with ciliary body cells, or more generally with a source of stem cells, according to the methods and systems of the present invention.

These and other aspects of the invention will become evident upon reference to the following detailed description and attached drawings. In addition, references set forth herein that describe in more detail certain aspects of this invention are therefore incorporated by reference in their entireties.

BRIEF DESCRIPTION OF THE SEVERAL VIEWS OF THE DRAWINGS

FIG. 2 illustrates survival of monkey retinal cells when co-cultured with monkey ciliary body cells and chicken embryonic cells. FIG. 2A presents a histogram showing the number of recoverin-expressing cells per 800,000 μm², with and without co-culture with embryonic chick retinal cells. FIG. 2B illustrates the number of monkey retinal cells that were immunohistochemically stained cells with an anti-recoverin antibody when the monkey cells were cultured alone, and FIG. 2C illustrates the number of monkey cells when co-cultured with embryonic chick retinal cells.

DETAILED DESCRIPTION OF THE INVENTION

Figure 1A:
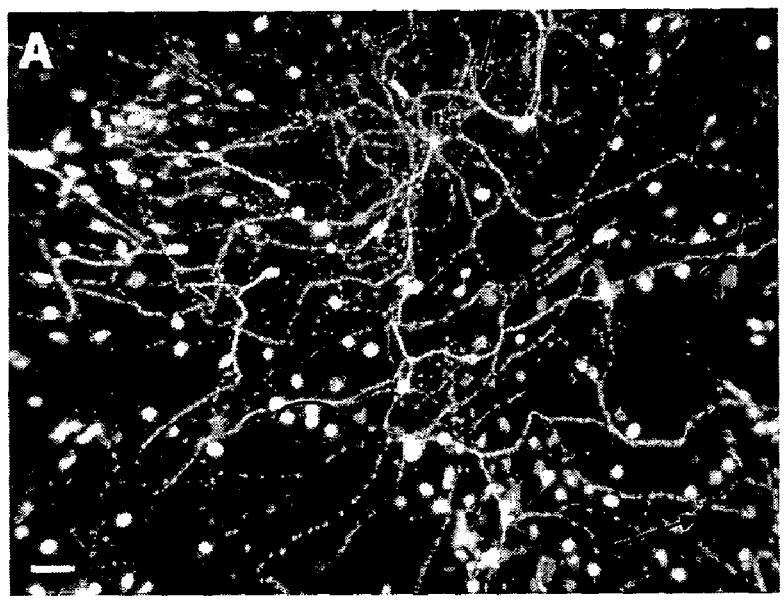
FIG. 1 illustrates immunohistochemical staining of monkey retinal cells and chicken retinal cells. Monkey retinal cells were cultured for 3 months (FIGS. 1A, 1B, and 1C). Chicken retinal cells were cultured for 14 days (FIG. 1D and FIG. 1E). Cells were subjected to immunological analysis using an anti-β3-tubulin antibody (FIGS. 1A, 1B, and 1E; representative cells are indicated by closed arrows) to identify ganglion cells, and using an antibody to calretinin to identify amacrine and horizontal cells (FIGS. 1A and 1E, representative cells are circled). The cells were stained with DAPI to identify the nuclei (muted staining in FIGS. 1A, 1B, 1D, and 1E; representatively stained cells are indicated by open arrow in FIGS. 1A, 1B, and 1D). Photoreceptor cells were identified with an antibody to recoverin (FIG. 1C; representative cells are circled); to visinin (D, representative cells are shown by open arrowhead); or to rhodopsin that stains the projections of the photoreceptor cells (FIGS. 1C and 1D; representative cells are circled). Scale bars: 20 μM.

Prior to setting forth the invention in detail, it may be helpful to the understanding thereof to define the following terms.

The term "neuron" is used herein to denote a cell that arises from neuroepithelial cell precursors. Mature neurons (i.e., fully differentiated cells from an adult) display several specific antigenic markers.

The term "ciliary body" is used herein to denote a tissue that resides between the peripheral regions of the retina and the iris, all of which arise from the same neuroepithelium during development.

The term "neuroepithelium" is used herein to denote cells and tissues that arise from the neural epithelium during development; such cells include retinal cells, diencephalon cells and midbrain cells. Neuroepithelium is also defined as neuroectoderm, and more specifically as ectoderm on the dorsal surface of the early vertebrate embryo that gives rise to the cells (neurons and glia) of the nervous system (On-line Medical Dictionary, Dept. of Medical Oncology, University of Newcastle upon Tyne; Mar. 4, 1998; Retrieved from the Internet: <URL:http://cancerweb.ncl.ac.uk/cgi-bin/omd?query=neuroepithelium&action=Search+OMD.

Neurodegenerative eye diseases, such as glaucoma and macular degeneration, affect nearly seventeen million patients in the United States alone. Considering the loss of quality of life associated with blindness, drug research and development in this area is of great importance.

Glaucoma is a broad term used to describe a group of diseases that causes visual field loss, often without any other prevailing symptoms. The lack of symptoms often leads to a delayed diagnosis of glaucoma until the terminal stages of the disease. Prevalence of glaucoma is estimated to be three million in the United States, with about 120,000 cases of blindness attributable to the condition. The disease is also prevalent in Japan with four million cases. In other parts of the world, access to treatment is even less, thus glaucoma ranks as a leading cause of blindness worldwide. Even if subjects afflicted with glaucoma do not become blind, their vision is often severely impaired. The loss of peripheral vision is caused by the death of ganglion cells in the retina. Ganglion cells are a specific type of projection neuron that connects the eye to the brain. Glaucoma is often accompanied by an increase in intraocular pressure. Current treatment includes use of drugs that lower the intraocular pressure. However, lowering the intraocular pressure is often insufficient to completely stop disease progression. It is believed that ganglion cells are quite susceptible to pressure and have already suffered permanent degeneration prior to the lowering of intraocular pressure. In addition, an increasing number of cases of normal tension glaucoma has been observed, in which ganglion cells degenerate without an observed increase in the intraocular pressure. Because current glaucoma drugs only treat intraocular pressure, a need exists to identify new therapeutic agents that will prevent or reverse the degeneration of ganglion cells. Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though it is often not thought of as part of the nervous system, retinal neurons are a key component of vision, interpreting the signals from the light sensing cells.

Macular degeneration is a disease that affects central vision, as opposed to glaucoma that affects peripheral vision. Prevalence of macular degeneration is estimated at thirteen million patients in the United States, and it is the leading cause of blindness worldwide. Macular degeneration is a disease that causes the loss of photoreceptor cells in the central part of retina, called the macula. Macular degeneration can be classified into two types: dry type and wet type. The dry form is more common than the wet, with about 90% of age-related macular degeneration (ARMD) patients diagnosed with the dry form. The wet form of the disease usually leads to more serious vision loss. The exact causes of age-related macular degeneration are still unknown. The dry form of ARMD may result from the aging and thinning of macular tissues, and deposition of pigment in the macula. With wet ARMD, new blood vessels grow beneath the retina and leak blood and fluid. This leakage causes the retinal cells to die, creating blind spots in central vision. The only FDA-approved protocol available to treat ARMD is a photodynamic therapy that uses a special drug combined with laser photocoagulation. This treatment, however, can only be applied to half of the new wet form cases of ARMD. For the vast majority of patients who have the dry form of macular degeneration, no treatment is available. Macula exists in primates (including humans), but not in rodents; therefore currently no good animal models of macula are available. This lack of a good animal model has proved to be a major obstacle for developing new drugs to treat this disorder.

Alzheimer's disease (AD) is the most common form of dementia among the elderly. Dementia is a brain disorder that seriously affects a person's ability to carry out daily activities. Alzheimer's is a disease that affects four million people in the United States alone. It is characterized by a loss of nerve cells in areas of the brain that are vital to memory and other mental functions. Some drugs can prevent AD symptoms for a finite period of time, but are no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

The present invention provides an in vitro neuronal cell culture system that will find use in the identification and biological testing of new neuroactive compounds or materials that may be suitable for treatment of neurological diseases or disorders in general, and for treatment of degenerative diseases of the eye and brain in particular. The cultured mature neurons provided herein are particularly useful for compound screening to identify candidate drugs that may enable regeneration of CNS tissue that has been damaged by disease. Neurodegenerative diseases or disorders for which the present invention may be useful for identifying agents that may treat, cure, prevent, ameliorate the symptoms of, or slow or stop the progression of, include but are not limited to glaucoma, macular degeneration, diabetic retinopathy, retinal detachment, retinal blood vessel (artery or vein) occlusion, retinitis pigmentosa, and retinal disorders associated with other neurodegenerative diseases such as Alzheimer's disease or Parkinson's Disease.

In addition, with the advent of novel technologies such as genomics and proteomics, thousands of new, relatively uncharacterized genes and proteins have been identified. One of the bottlenecks of drug discovery and development is determining how to prioritize thousands or millions of small molecule and proteinaceous therapeutic agent candidates that are available for high-throughput screening. Most of these high-throughput assay systems are based on test molecule stimulation or inhibition of target cell enzymatic activity, or on test molecule binding to a target molecule or target cell. Because in vivo systems feature complex interactions between target molecules or target cells and surrounding molecules within the target molecule's cellular environment, or the target cell's surrounding tissue environment, it is hard to predict how a candidate molecule, identified by an isolated biochemical assay, will exert its influence in an in vivo setting. For example, certain target proteins, such as transcription factors and cell-surface receptors, often form multi-subunit complexes in order to exhibit biological function. Furthermore, the response of a target protein to potential therapeutic agents is likely to be dependent on its cellular context. An assay using the cultured neurological cells provided by the present invention will better mimic the in vivo target molecule environment.

Another research and development bottleneck involves correlating genetic analysis or sequence information to functional biology in order to validate a target. Bioinformatics and genomic technologies have identified new genes that map to regions of the chromosome associated with genetic mutations or defects that have been associated with biological diseases or disorders. However, identifying and analyzing the precise biological function of the thousands and millions of interesting genes (and their corresponding gene products) is proving to be extremely challenging. Without good cellular models, it is difficult to elucidate the true biological function of each protein. Thus, although bioinformatics and genomics techniques can now quickly identify potential disease-causing proteins and candidate therapeutic agents, characterizing the biological significance and function of each such molecule continues to be difficult and time consuming. Consistent and reproducible cell-based assay systems, such as provided herein, will accelerate this functional analysis. Further, use of the cultured neuronal cells of the present invention may permit identification of bioactive agents that target intracellular functional units or other types of non-protein molecules, such as ribosomes, lipids, or carbohydrates.

The next generation of drug discovery platform technology may incorporate "cellomics." Cellomics will utilize comprehensive analyses of in vitro cultured cells. Cell-based screening systems will allow candidate biopharmaceutical agents to interact with corresponding target molecules in a more physiological state than simple protein-target analysis.

In one embodiment, the present invention provides methods for culturing retinal neurons in vitro for extended periods of time, preferably longer than 2 weeks or 4 weeks, more preferably longer than 2 months, and still more preferably longer than 3 months. Retinal neurons have been obtained from post-natal non-human primates and post-natal chickens, but any adult or post-natal retinal tissue may be suitable for use within the present invention. The source of the retinal cells or tissue may be mammalian (e.g., human, non-human primate, rodent, canine, porcine, bovine, or other mammalian source), avian, or from other genera.

The types of retinal neuronal cells that may be cultured in vitro by this method include ganglion cells, photoreceptors, bipolar cells, horizontal cells, and amacrine cells. A feature of this invention is co-culture of retinal neurons with ciliary body cells, and/or with a source of stem cells. The ciliary body is a tissue in the eye that includes the group of muscles that act on the eye lens to produce accommodation and the arterial circle of the iris. The inner ciliary epithelium is continuous with the pigmented retinal epithelium, and the outer ciliary epithelium secretes the aqueous humour. The pigmented epithelium from the ciliary body is reported to include retinal stem cells (Tropepe et al., *Science* 287:2032-36 (2000); Fischer et al., *Develop. Biol.* 220:197-200 (2000)). Although ciliary body-derived cells are preferred, sources of CNS-derived stem cells may also be used within the invention. Adult or post-natal ciliary body cells are preferred. Embryonic cells, particularly, retinal embryonic cells may be used in the cell culture system and include embryonic stem cells and embryonic neuronal progenitor cells. Sources of adult, embryonic or pre-natal stem cells (retinal stem cells or non-retinal stem cells; CNS-derived stem cells or stem cells derived from other tissue types; mammalian-, avian- or other genera- and species-derived stem cells) may also be used. The source of the stem cells, including the source of the retinal stem cells, may be primary cells, or may be immortalized, transformed, tumorigenic, or genetically manipulated cells that can be cultured in vitro indefinitely.

The present invention provides an effective method for identifying and analyzing bioactive agents in general, and neuroactive agents in particular. Through use of such method, agents useful for treating diseases and disorders of the central nervous system and retina, including but not limited to neurodegenerative diseases, epilepsy, macular degeneration, and glaucoma, may be selected and tested. According to the present invention, a bioactive agent may include, for example, a peptide, a polypeptide (for example, a ligand that binds to a neuronal cell receptor, a growth factor, trophic factor, or the like), an oligonucleotide or polynucleotide, antibody or binding fragment thereof, or small molecule. Candidate agents for use in a method of screening for a bioactive agent that is capable of altering (increasing or decreasing in a statistically significant manner) neurodegeneration of neuronal cells, such as retinal neuronal cells, may be provided as "libraries" or collections of compounds, compositions, or molecules. Such molecules typically include compounds known in the art as "small molecules" and having molecular weights less than $10^5$ daltons, preferably less than $10^4$ daltons and still more preferably less than $10^3$ daltons. Preferably, a bioactive agent inhibits, impairs, or prevents neurodegeneration of neuronal cells. Candidate agents further may be provided as members of a combinatorial library, which preferably includes synthetic agents prepared according to a plurality of predetermined chemical reactions performed in a plurality of reaction vessels. The resulting products comprise a library that can be screened and then followed by iterative selection and synthesis procedures, to provide, for example, a synthetic combinatorial library of peptides (see, e.g., PCT/US91/08694, PCT/US91/04666) or other compositions that may include small molecules as provided herein (see, e.g., PCT/US94/08542, U.S. Pat. No. 5,798,035, U.S. Pat. No. 5,789,172, U.S. Pat. No. 5,751,629). Those having ordinary skill in the art will appreciate that a diverse assortment of such libraries may be prepared according to established procedures.

The present invention provides methods for identifying bioactive agents that may be useful for treating neurodegenerative diseases, including but not limited to retinal diseases such as glaucoma, macular degeneration, diabetic retinopathy, retinal detachment, retinal blood vessel (artery or vein) occlusion, retinitis pigmentosa, and retinal disorders associated with other degenerative diseases such as Alzheimer's disease. Bioactive agents as described herein may be incorporated into screening assays comprising the subject invention cell culture system to determine whether a bioactive agent is capable of altering neurodegeneration of neuronal cells (impairing, inhibiting, preventing, or accelerating in a statistically significant manner). A preferred bioactive agent is one that inhibits or impairs neurodegeneration of a neuronal cell or that is capable of regenerating a neuronal cell. A bioactive agent that inhibits neurodegeneration of a neuronal cell may be identified by contacting (mixing, combining, or otherwise permitting interaction between the agent and cells of the cell culture system), for example, a candidate agent from a library of agents as described herein, with the cell culture system under conditions and for a time sufficient to permit interaction between a candidate agent and the cells, particularly the mature neuronal or retinal neuronal cells of the cell culture system. A bioactive agent may act directly upon a neuronal or retinal neuronal cell to affect survival or neurodegeneration of the cell. Alternatively, a bioactive agent may act indirectly by interacting with one cell that consequently responds to the agent by affecting survival or neurodegeneration of another neuronal cell.

A bioactive agent that effectively alters, preferably inhibits, neurodegeneration of a neuronal cell may be identified by techniques known in the art and described herein for determining the effects of the agent on neuronal cell structure or morphology; expression of neuronal cell markers (e.g., β3-tubulin, rhodopsin, recoverin, visinin, calretinin, Thy-1, tau, microtubule-associated protein 2, and the like (see, e.g., Espanel et al., *Int. J. Dev. Biol.* 41:469-76 (1997); Ehrlich et al., *Exp. Neurol.* 167:215-26 (2001); Kosik et al., *J. Neurosci.* 7:3142-53 (1987))); and/or cell survival (i.e., cell viability or length of time until cell death). Preferably, a bioactive agent enhances survival of neuronal cells such as retinal neuronal cells, that is, the agent promotes survival or prolongs survival such that the time period in which neuronal cells are viable is extended. The ability of a candidate agent to enhance cell survival or impair, inhibit, or impede neurodegeneration may be determined by any one of several methods known to those skilled in the art. For example, changes in cell morphology in the absence and presence of a candidate agent may be determined by visual inspection such as by light microscopy, confocal microscopy, or other microscopy methods known in the art. Survival of cells can be determined by counting viable and/or nonviable cells, for instance. Immunochemical or immunohistological techniques (such as fixed cells staining or flow cytometry) may be used to identify and evaluate cytoskeletal structure (e.g., by using antibodies specific for cytoskeletal proteins such as synapsin, an intermediate filament protein such as glial fibrillary acidic protein, fibronectin, actin, vimentin, tubulin, or the like) or to evaluate expression of cell markers as described herein. The effect of a candidate agent on cell integrity, morphology, and/or survival may also be determined by measuring the phosphorylation state of neuronal cell polypeptides, for example, cytoskeletal polypeptides (see, e.g., Sharma et al., *J. Biol. Chem.* 274:9600-06 (1999);

Li et al., *J. Neurosci.* 20:6055-62 (2000)). Regeneration of neuronal cells or proliferation of neuronal cells may be determined by any of several methods known in the art, for example, by measuring incorporation of labeled deoxyribonucleotides or ribonucleotides or derivatives thereof, such as tritiated thymidine, or such as by measuring incorporation of bromodeoxyuridine (BrdU), which can be detected by using antibodies that specifically bind to BrdU.

In some situations, such methods may enable identification of candidate therapeutic agents that not only improve the symptoms of neurodegeneration, but also act to reverse the state of neurodegeneration. The disclosed methods and cell culture systems permit very precise measurements of specific interactions occurring between neurons, as well as enabling detailed analysis of subtleties in neuron structure. For instance, the methods and cultured cells of the present invention are compatible with neurochips, cell-based biosensors, and other multielectrode or electrophysiologic devices for stimulating and recording data from cultured neurons (see, for instance, M. P. Maher et al., *J. Neurosci. Meth.* 87:45-56, 1999; K. H. Gilchrist et al., *Biosensors & Bioelectronics* 16:557-64, 2001).

Screening Neurological Targets for Drug Discovery

Neurodegenerative diseases are a major source of morbidity, and an in vitro neural cell culture model may benefit drug discovery in this area. Because culturing of postmitotic neuronal cells has been so difficult, it is critical to have a good paradigm when screening drugs relevant to neurologic and ophthalmic diseases. As noted previously, the response of target molecules to potential drug candidates is likely to be dependent on the cellular environment of the target molecule. Thus, it is important to use in screening assays cultured cells that are closely related to the cell types that are to be ultimately treated with the drug.

To properly validate drug/therapeutic agent candidates, tissue-specific cultured cells for use within a cell-based screening system must be identified and evaluated. In the field of neurobiology, cell lines such as PC12 cells (derived from a rat pheochromocytoma), NT2 cells (derived from a human teratocarcinoma), or human neuroblastoma cell lines have been used to screen drug candidates. While these cells have some characteristics of prototypic neurons, these cells are tumor-derived, and have an immature neuronal phenotype considered to be different from physiological neural cells.

In Vitro Cell Culture System

Others groups have reported in vitro culture of embryonic retinal neurons, but these cells fail to express all of the retina-specific proteins that are expressed by mature retinal cells, or these cells could only be cultured for short times. X. Luo et al. (*IOVS* 42:1096-1106, 2001) have reported culturing of retinal cells in vitro, but their system differed from the one disclosed herein in that the in vitro cell culture system of the present invention includes co-culture with ciliary body cells (or with a source of stem cells).

Only one group has reported that adult and aged human, porcine, and rodent retinal neurons survived in monolayer culture conditions (Gaudin et al., *Investig. Ophthalmol. & Visual Sci.* 37:2258-68, 1996). This group reported that photoreceptor cells regenerated neuritic processes in association with underlying glia, which were stated to be essential for their long term survival and neuritogenesis. Gaudin et al. estimated that porcine retinal cells exhibited survival of 5-10% for originally seeded neurons after 10 days in vitro; rat retinal cells exhibited survival of ~1% for originally seeded neurons after 2 weeks in vitro; and human retinal cells exhibited survival of ~1% for originally seeded neurons after 2 months in vitro.

The neuronal cell culture system disclosed herein differs from previous systems in that cells isolated from a ciliary body (and/or a source of stem cells) are included with mature neuronal cells as part of an in vitro culture environment. A preferred in vitro cell culture system of the present invention includes all of the major retinal neuronal cell types in the culture (photoreceptor cells, bipolar cells, horizontal cells, amacrine cells, and ganglion cells), and also includes mature retinal neurons. By incorporating these different types of cells into the disclosed in vitro culture system for maintenance of mature retinal neurons, the system essentially resembles an "artificial organ" that is more akin to the natural in vivo state. In one embodiment of the invention, the cell culture system of the present invention is a mixture of mature retinal and cells isolated from a ciliary body. Cells may be isolated by mechanical means, such as dissection and teasing (triturating) or by more rigorous mechanical methods, such as sonication. Tissues of the eye may also be treated with enzymes such as hyaluronidase, collagenase, and a deoxyribonuclease, to dissociate the cells. Preferably, the subject invention cell culture system is prepared by a combination of mechanical methods and enzymatic digestion. The cell culture system also comprises media, nutrients, and conditions such as temperature and an appropriate mix of gases, that are required for in vitro culture of cells and that are well known in the art.

In certain embodiments of the invention, the neuronal cell culture system comprises a mixture of mature neuronal cells such as mature retinal neuronal cells, cells isolated from a ciliary body, and embryonic retinal cells. Embryonic retinal cells include, for example, retinal stem cells and embryonic retinal progenitor cells. A neuronal progenitor cell has the ability to differentiate into a cell that has a defined morphology and histological type. Embryonic progenitor cells include undifferentiated cells that display a high proliferative potential and may generate a wide variety of differentiated progeny including the major cell phenotypes of a tissue. (See Gage et al., *Annu. Rev. Neurosci.* 18:159-92 (1995)). Retinal progenitor cells include cells that differentiate into any one of the five types of mature retinal cells (photoreceptors, bipolar cells, horizontal cells, amacrine cells, and ganglion cells). Stem cells are capable of dividing into a progenitor cell and another stem cell. Progenitor cells may also be derived from adult retina tissue. The mixture of co-cultured cells may also include stem cells isolated from the central nervous system, preferably retinal stem cells, which may be embryonic or adult-derived retinal stem cells. Embryonic progenitor cells and CNS stem cells including retinal stem cells may be obtained from a mammalian source (e.g., a human, non-human primate, rodent, pig, or other mammal), an avian source (e.g., chicken), or other animal.

This in vitro culture system may serve as a physiological retinal model that can be used to characterize the physiology of the retina in vitro in large numbers. This physiological retinal model may also be used as a broader model of general neurobiology, and disease models may be built upon this technology by adding various stressors, such as glucose oxygen deprivation, pressure, light exposure, various toxins or combinations of these. A chronic disease model is of particularly importance because most neurodegenerative diseases are chronic. Through use of this in vitro cell culture system, the earliest events in long-term disease development processes may be identified because an extended period of time is available for cellular analysis.

The disclosed mixed culture system may lend itself to the identification of both direct and indirect pharmacologic agent effects. For example, some drug candidates may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

This in vitro cell culture system may also be used as a model system to permit identification of bioactive molecules that allow neurons to survive. In addition, this in vitro cell culture system may be useful for investigating long term effects of bioactive molecules that may not exhibit their effects during short time frames. Further, this system may find use in detecting and/or identifying various toxins or neurotoxins. The availability of a long-term cell culture system may be particularly beneficial in the field of neurotoxicology because some chemicals and active agents have toxic effects in low doses, but only over extended periods of time.

The subject invention cell culture system described herein may be used as an in vitro model to identify and to evaluate cell types that may be useful for treatment of neurodegenerative diseases and disorders. In one embodiment of the present invention, various neuronal cell types are added to a mixture of retinal neuronal cells (or other neuronal cells) and cells isolated from a ciliary body. As disclosed herein, in this cellular model, adding embryonic retinal cells or retinal stem cells to the mixture of cells can increase the number of surviving retinal neuronal cells by preventing cell death, such as photoreceptor cells, thus indicating that retinal stem cells may be useful for treating degenerative retinal diseases. For treatment of retinal disorders and dysplasias, transplantation of neural progenitor cells has been investigated (see, e.g., WO 00/47238; Seiler et al., Invest. *Ophthalmol. Vis. Sci.* 39:2121-31 (1998)); Aramant et al., *Restor. Neurol. Neurosci.* 2:9-22 (1990)). Whereas the descendents of progenitor cells can differentiate along a particular pathway to a fully differentiated phenotype, stem cells are capable of dividing into a progenitor cell and another stem cell, thus providing a potential continuing source of cells to replace damaged or dying cells.

This invention therefore relates to the discovery that retinal stem cells may be useful for treating neurodegenerative diseases and disorders, particularly neurodegenerative retinal diseases as described herein. A subject in need of such treatment may be a human or non-human primate or other animal and who has developed symptoms of a neurodegenerative retinal disease or who is at risk for developing a neurodegenerative disease. Treating such a subject is understood to encompass preventing further cell death, or replacing, augmenting, repairing, or repopulating damaged tissue and cells by administering retinal stem cells. Preferably, the retinal stem cells are administered to a subject in need thereof prior to the end-stage of a neurodegenerative disease, and preferably at a time point prior to initiation of neurodegeneration or at a time point that will prevent, slow, or impair further neurodegeneration (that is, for example, soon after an initial diagnosis has been made). By way of example, a diagnosis of macular degeneration can be made at early stages of the disease. According to the present invention, introduction of retinal stem cells at the time of diagnosis may delay, prevent, impair, or inhibit further neurodegeneration of retinal neuronal cells by preventing photoreceptor cell death. While retinal stem cells are preferred, another source of stem cell, particularly other central nervous system stem cells may also be used.

The stem cells may be introduced into a subject in need thereof according to standard transplantation procedures known in the medical arts, including grafting, near or at the site of dystrophic tissue, preferably into retinal tissue, and may also include injection of retinal stem cells into a site, for example, into the vitreous of the eye. The transplantation may be an autograft (stem cells from the subject to be treated); syngeneic graft (of the same strain, that is, having the same histocompatibility genes); allogeneic graft (same species, but different strains, that is, the donor and recipient have different histocompatibility genes); or xenogenic graft (donor and recipient belong to different species or genus). For transplantation in humans, non-human primates may be used as a source of stem cells. Alternatively, transgenic animals, such as a transgenic pig, may be an acceptable source of retinal stem cells. Procedures and methods for increasing the likelihood that a tissue graft will not be rejected (i.e., decreasing or abrogating the immune response of the recipient to the transplanted tissue) by the subject are well known in the art.

The methods and systems of the present invention may also be used to provide a source of neuronal cell RNA and DNA. For instance, the neuronal cells cultured according to the described methods and systems may provide sufficient and appropriate material for construction of neuronal cell cDNA libraries. In addition, such neuronal cell cultures may be useful in proteomics analyses.

The methods and systems of the claimed invention may find use as a biosensor to detect molecules used for bioterrorism, and particularly as a biosensor to detect neurologically active molecules of bioterrorism. The disclosed methods and systems may also be used to identify and develop therapeutic agents that are capable of counteracting the effects of such molecules of bioterrorism.

The beneficial effect provided by combining ciliary body cells (and/or stem cells) with mature neuronal cells may also be used to support extended culture of non-retinal neurons (for instance, other central nervous system and peripheral nervous system neurons). In addition, cells other than ciliary body cells (for instance, non-retinal stem cells or other CNS-derived stem cells) may be advantageously combined in co-culture with various types of neuronal cells within the in vitro cell culture system of the present invention.

Embryonic retinal stem cells also enhanced the survival of primate photoreceptors under co-culture conditions. Combinations of factors, such as ciliary neurotrophic factor (CNTF), brain-derived neurotrophic factor (BDNF), fibroblast growth factor-2 (FGF2), and glial cell line-derived neurotrophic factor (GDNF) have been reported to improve the survival of photoreceptors in organ cell culture systems (J. M. Ogilvie et al., *Exp. Neurol.* 161:676-85, 2000), but none of these factors sustain survival of neuronal cells for the period of time achievable with the in vitro cell culture system of the present invention. The in vitro cell culture system provided herein may be useful in detecting and identifying additional trophic factors that enhance survival of mature retinal neurons.

Platform

The in vitro cell culture system described herein permits the survival in culture of mature primate retinal neurons for over two months. Until now, the ability to screen drug candidates using mature retinal neurons has been limited to the life span of the neurons in primary culture. Delays in enucleation and delays in tissue dissociation have a severe deleterious effect on recovery and survival of neurons (see, for example, Gaudin et al, supra). Neurons begin to deteriorate immediately after being dissociated from neural tissue. The resulting deterioration of the neurons prevents adequate compound screening by the pharmaceutical industry. Also, at present, it is difficult to analyze projection neuron or photoreceptor cells. Photoreceptors are the primary cell type affected in macular degeneration, a leading cause of blindness. Ganglion cells are projection neurons in the retina; these cells are affected in glaucoma patients, also a leading cause of blindness.

Through use of the methods of the present invention, retinal neurons may be cultured in vitro for extended periods of time, enabling fully mature neurons to survive for a period of over two months. The ability to culture the photoreceptors and associated ganglion projection neurons for extended periods of time enables screening of compounds that influence retinal disease. The disclosed methods and cell culture systems may also be applicable to brain and spinal cord diseases.

The methods and systems described herein may also be applied to mature neuronal cells obtained from genetically mutated animal models. For instance, mature neurons may be obtained from an animal that expresses the retinal dystrophic (rd/rd) allele. A comparison of wild-type and mutant neuronal cells in extended cell culture conditions may aid in identification of bioactive molecules, or in identification of up- or down-regulated moieties within these cells upon exposure to stresses or added/subtracted compounds or nutrients. Other animal models that carry characterized alleles relating to brain, eye, or other CNS disorders or diseases may be amenable for use as a source of mature differentiated cells (including mature neuronal cells) within the claimed methods and systems.

The cell culture systems and methods of the present invention may be used in conjunction with any glass surface (including, for instance, coverslips) that has been coated with an attachment-enhancing substance, such as poly-lysine, Matrigel, laminin, polyornithine, gelatin and/or fibronectin. Feeder cell layers, such as glial feeder layers or embryonic fibroblast feeder layers, may also find use within the methods and systems provided herein.

Thus, the present invention provides methods for extended culture of mature neuronal cells that features incubating mature neuronal cells with ciliary body cells (and/or with a source of stem cells). The present invention further provides an in vitro cell culture system that features a mixture of mature neuronal cells and ciliary body cells (and/or a source of stem cells). Also, a method for screening bioactive molecules, using an in vitro cell culture system containing a mixture of mature neuronal cells and ciliary body cells (and/or a source of stem cells), is provided.

The invention is further illustrated by the following non-limiting examples.

EXAMPLES

Example 1

Preparation of Retinal Neuronal Cell Culture System

All compounds and reagents were obtained from Sigma Chemical Corporation (St. Louis, Mo.), except as noted.

Source of Tissue

Eyes of *Macaca nemestrina* and *Macaca fascicularis* were obtained from the Regional Primate Research Center at the University of Washington (Seattle, Wash.) through the Tissue Distribution Program. The use of animals in these experiments was in accordance with the guidelines established by the National Institute of Health and the University of Washington Animal Care Committee. Monkeys aged 4 to 17 years were used (monkeys are fully mature at 4 years old) as a source of retinal tissue. Chickens were housed in clear Nalgene cages at approximately 25° C. The chickens received water and Purina chick starter ad libitum, and were maintained on a cycle of 16 hours light, 8 hours dark (lights on at 6:00 AM). Chickens were sacrificed through use of chloroform overanaesthesia, and the eyes were enucleated.

Tissue Preparation and Cell Culture

Enucleated eyes were cut in half along their equator, and the neural retina (including or excluding the ciliary body) was dissected from the anterior part of the eye in Hank's buffered saline solution (HBSS; Gibco BRL) with 1 mM Hepes buffer (pH 7.4) and 2% sucrose. Each retina was dissociated with 15 minutes of incubation at 37° C. in 5 ml of $Ca^{2+}$-, $Mg^{2+}$-free HBSS containing 0.125% trypsin (Gibco BRL, Invitrogen Life Technologies, Carlsbad, Calif.), 100 U/ml hyaluronidase, 10 U/ml collagenase, and 0.1 mg/ml Dnasel, followed by inactivation with 5% fetal bovine serum (FBS; Gibco BRL). The enzymatically dissociated cells were triturated 10 times with a 5-ml plastic pipette, and then triturated 20 times with a fire-polished glass pipette. Dissociated cells were collected by centrifugation for 10 min at 1500×g, resuspended in Dulbecco's modified Eagle's medium (DMEM)/F12 medium (Gibco BRL) containing 25 µg/ml of insulin, 100 µg/ml of transferrin, 60 µM putrescine, 30 nM selenium, 20 nM progesterone, 100 U/ml of penicillin, 100 µg/ml of streptomycin, 0.05 M Hepes, and 1% FBS. Cells were plated onto glass coverslips coated with poly-D-lysine and Matrigel (Becton Dickinson Biosciences, Franklin Lakes, N.J.) at 200,000 cells per well in 24-well plates. One half of the media in each well was changed every 48 hours. Cells were incubated at 37° C. and 5% $CO_2$, and maintained from 14 days to 3 months. In some cases, E6 chicken embryonic retinal cells (300,000 cells per well of a 24-well plate) were plated onto the coated coverslips 1 day before the mature monkey ciliary body cells and retinal cells were plated. Briefly, to obtain E6 chicken embryonic retinal cells, eggs were obtained from H&N International WA and were kept in a humidified incubator for 6 days (corresponding to embryonic day 6 or "E6"). Day 6 embryos were removed from the eggs, and the embryonic retinal cells were obtained and plated, as described above.

Example 2

Immunocytochemical Analyses of Cultured Cells

Immunocytochemical analysis of cultured retinal cells was performed according to methods well known in the art. Rod photoreceptors were identified by labeling with the rhodopsin-specific antibody 4D2 (diluted 1:1000; provided by Dr. R. Moday, University of British Columbia, Vancouver, British Columbia, Canada). The Tuj1 antibody, which recognizes β3-tubulin (and is specific to ganglion cells), was used to identify ganglion cells. A primate-specific (i.e., does not bind to chicken cells or tissue) antibody to recoverin (diluted 1:1000; provided by Dr. J. Hurley, University of Washington, Seattle, Wash.) was used to identify primate photoreceptor cells. Antibodies to visinin were used to identify chicken photoreceptor cells. An antibody to bromodeoxyuridine (BrdU, diluted 1:80; Developmental Studies Hybridoma Bank, University of Iowa, Iowa City, Iowa) was used to identify BrdU-containing cells. Nuclei were stained with 4',6-diamidino-2-phenylindole (DAPI). To detect the immunoreactivity of the primary antibodies, Alexa 488- or Alexa 568-conjugated goat antibodies (Molecular Probes, Eugene, Oreg.) were used. Images were acquired with a Spot slider-RT camera (Diagnostic Instruments, Inc., Michigan) attached to an Axioplan2 microscope (Carl Zeiss, New York).

Example 3

Analyses of Enhanced Survival of Neuronal Cells

Figure 1B:
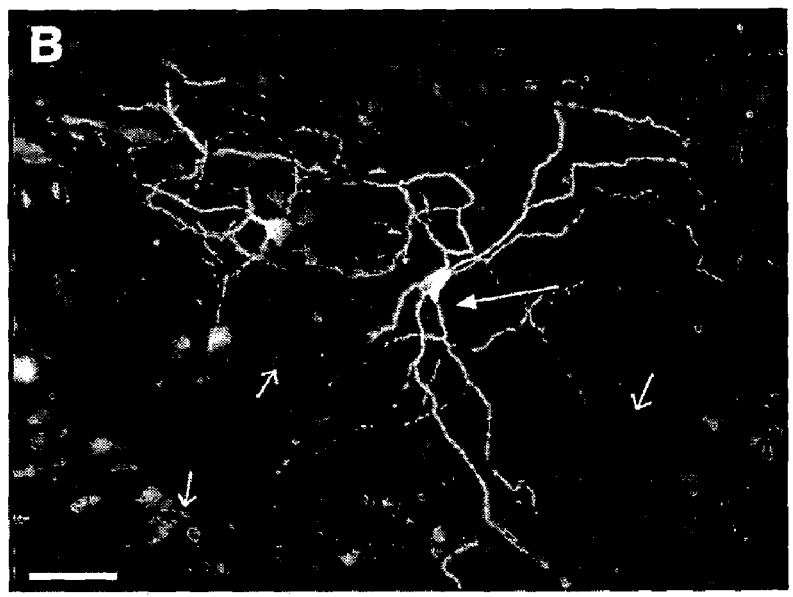
Figure 1C:
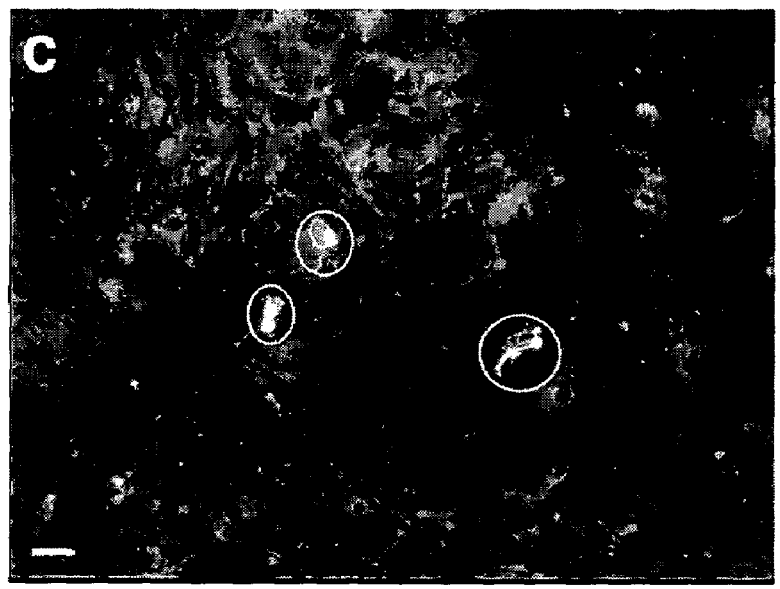

When mature retinal neurons were cultured in the absence of the epithelium of the ciliary body, all of the retinal neurons perished in 1 or 2 days. When ciliary body cells were co-cultured with mature retinal neurons (under identical conditions as those used for culture of mature neurons in the absence of the epithelium of the ciliary body), various neurons were identified by immunocytochemical techniques as described in Example 2. As these cultures were maintained for extended time period, the continued survival of retinal neurons was observed. FIGS. 1A-C illustrates survival of primate mature retinal neurons after 3 months of in vitro culture. The presence of viable cells was confirmed by staining of the nuclei with DAPI (see FIGS. 1A and 1B; muted staining with representative cells indicated by an open arrow). Immunostaining with a labeled anti-β3-tubulin antibody shows the presence of ganglion cells in the long term culture (FIGS. 1A and 1B; representative cells are indicated by a closed arrowhead). Amacrine and horizontal cells were identified by immunostaining with an antibody that is specific for calretinin (FIG. 1A; representative cells are circled). Photoreceptor cells present in the culture were identified by immunohistochemistry using an anti-recoverin antibody and an anti-rhodopsin antibody (FIG. 1C; representative cells are circled).

Figure 1D:
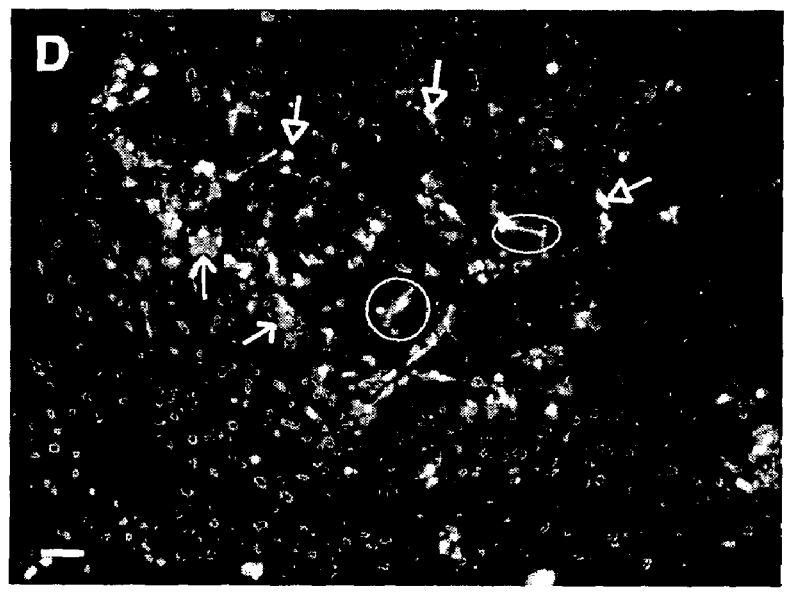
Figure 1E:
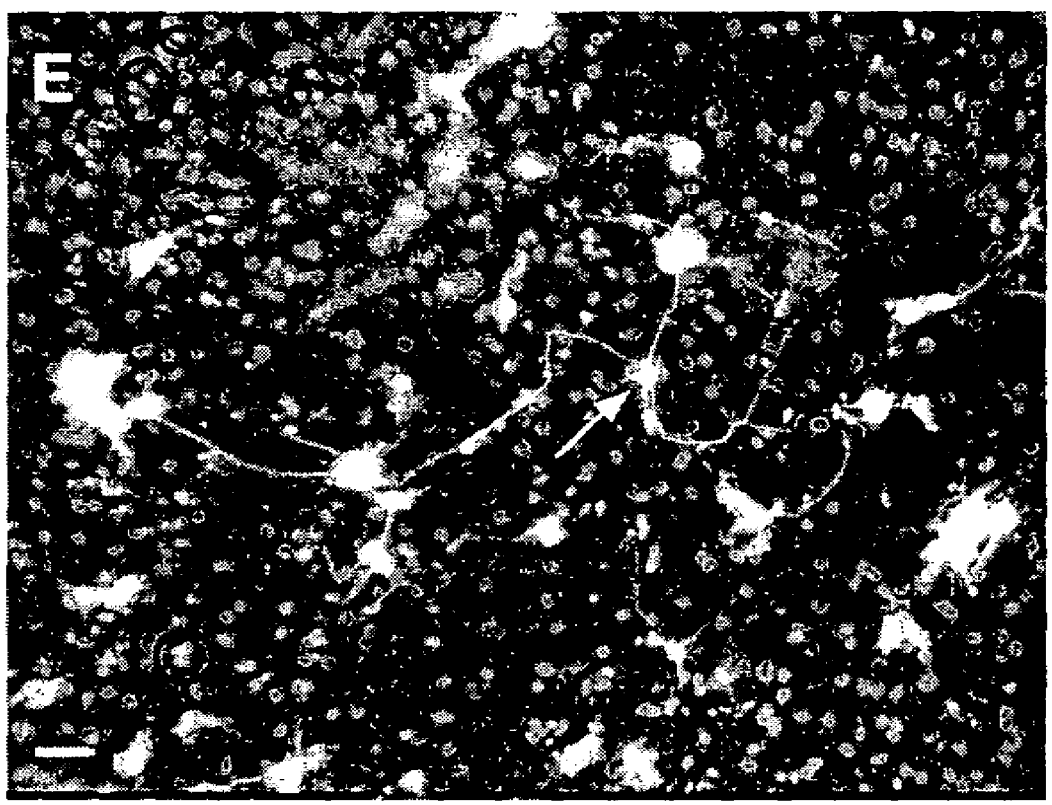

To analyze whether this enhancement of survival applied to other species of retinal neurons, chicken retinas were cultured in a similar manner. When mature chicken retinal cells were co-cultured with cells from the chicken ciliary body, chicken retinal neurons survived for at least 12 days. Immunocytochemical analyses were performed as described in Example 2. Immunostaining with an anti-β3-tubulin indicated the presence of ganglion cells (FIG. 1E). Photoreceptor cells were identified by immunostaining with an anti-visinin antibody and an anti-rhodopsin antibody (FIG. 1D). Amacrine and horizontal cells that were present in the culture were identified by immunostaining with an antibody that is specific for calretinin (FIG. 1E; representative cells are circled). Nuclei of cells were indicated by staining with DAPI (see FIGS. 1D and 1E). In contrast, when mature chicken retinal cells were cultured in the absence of chicken ciliary body cells, no chicken retinal neurons survived until the next day. Thus, ciliary body cells promote the survival of retinal neurons obtained from a variety of species. Ciliary body cells contain retinal stem cells in rodents and birds (Tropepe et al., *Science* 287:2032-36, 2000; Fischer et al., *Develop. Biol.* 220:197-200, 2000).

To determine whether the surviving mature neurons were newly generated cells, 1 µM BrdU was added to the cultures after plating. No BrdU-labeled neurons were detected, indicating that the surviving neurons were derived from the mature retinal neurons that were dissociated and cultured under the described experimental conditions.

To determine whether embryonic retinal stem cells were capable of promoting the survival of mature retinal neurons, E6 chicken embryonic retinal cells (300,000 cells per 24-well plate well) were added to the culture 1 day before plating mature monkey ciliary body cells and retinal cells. An increase in the number of recoverin-immunoreactive retinal neurons was observed. The antibodies to recoverin that were used bind to primate rod and cone photoreceptors, but do not bind to any chicken cell types. More specifically, recoverin-immunoreactive cells increased from 8.6 to 78.9 cells per 800,000 µm$^2$ when embryonic chicken retinal cells were added as a source of stem cells (FIG. 2A). An almost 10-fold increase in the number of surviving photoreceptors was observed (FIGS. 2B and 2C).

From the foregoing, it will be appreciated that, although specific embodiments of the invention have been described herein for purposes of illustration, various modifications may be made without deviating from the spirit and scope of the invention.

We claim the following:

1. A retinal cell culture system comprising a mixture of (i) mature retinal neuronal cells; (ii) cells isolated from a ciliary body; and (iii) embryonic retinal cells, wherein the mature retinal neuronal cells are isolated from retinal tissue, and wherein the mature retinal neuronal cells comprise a bipolar cell, a horizontal cell, an amacrine cell, a ganglion cell, and a photoreceptor cell.

2. The cell culture system of claim 1 wherein the embryonic retinal cells comprise retinal stem cells.

3. The cell culture system of claim 1 wherein the embryonic retinal cells comprise embryonic retinal progenitor cells.

4. A method for producing a retinal cell culture system comprising co-culturing (i) mature retinal neuronal cells; (ii) cell isolated from a ciliary body; and (iii) embryonic retinal cells, wherein the mature retinal neuronal cells are isolated from retinal tissue, and wherein the mature retinal neuronal cells comprise a bipolar cell, a horizontal cell, an amacrine cell, a ganglion cell, and a photoreceptor cell.

5. The method according to claim 4 wherein the embryonic retinal cell is selected from a retinal stem cell and an embryonic retinal progenitor cell.

6. A method for identifying a bioactive agent that is capable of enhancing survival of a mature retinal neuronal cell, comprising (i) contacting a candidate agent with a cell culture system according to claim 1, under conditions and for a time sufficient to permit interaction between a mature retinal neuronal cell of the cell culture system and the candidate agent; and (ii) comparing survival of a mature retinal neuronal cell of the cell culture system in the presence of the candidate agent with survival of a mature retinal neuronal cell of the cell culture system in the absence of the candidate agent, and therefrom identifying a bioactive agent that is capable of enhancing survival of the mature retinal neuronal cell.

7. A method for identifying a bioactive agent that is capable of inhibiting neurodegeneration of a mature retinal neuronal cell comprising (i) contacting a bioactive agent with a cell culture system according to claim 1, under conditions and for a time sufficient to permit interaction between a mature retinal neuronal cell of the cell culture system and the candidate agent; and (ii) comparing structure of a mature retinal neuronal cell of the cell culture system in the presence of the bioactive agent with structure of a mature retinal neuronal cell of the cell culture system in the absence of the bioactive agent, and therefrom identifying a bioactive agent that is capable of inhibiting neurodegeneration of the mature retinal neuronal cell.

8. A method for identifying a bioactive agent that is capable of treating a retinal disease comprising contacting a bioactive agent with a cell culture system according to claim 1, under conditions and for a time sufficient to permit interaction between a mature retinal neuronal cell of the cell culture system and the candidate agent; and (ii) comparing neurodegeneration of a mature retinal neuronal cell of the cell culture system in the presence of the bioactive agent with neurodegeneration of a mature retinal neuronal cell of the cell culture system in the absence of the bioactive agent, and therefrom identifying a bioactive agent that is capable of treating a retinal disease.

9. The method of claim 8 wherein the retinal disease is selected from the group consisting of macular degeneration, glaucoma, diabetic retinopathy, retinal detachment, retinal blood vessel occlusion, retinitis pigmentosa, and a retinal disorder associated with Alzheimer's disease.

* * * * *

UNITED STATES PATENT AND TRADEMARK OFFICE
CERTIFICATE OF CORRECTION

| | | |
|---|---|---|
| PATENT NO. | : 7,312,025 B2 | Page 1 of 1 |
| APPLICATION NO. | : 10/618076 | |
| DATED | : December 25, 2007 | |
| INVENTOR(S) | : Ryo Kubota et al. | |

It is certified that error appears in the above-identified patent and that said Letters Patent is hereby corrected as shown below:

In the Claims:

In Column 16, line 38 (Claim 4), please replace "a cell" with --cells--.

Signed and Sealed this

Eleventh Day of November, 2008

JON W. DUDAS
*Director of the United States Patent and Trademark Office*